United States Patent [19]

Golub et al.

[11] Patent Number: 5,459,135
[45] Date of Patent: Oct. 17, 1995

[54] COMPOSITION COMPRISING INDOMETHACIN [NON-STEROIDAL ANTI-INFLAMMATORY AGENT] AND EFFECTIVELY NON-ANTIBACTERIAL TETRACYCLINE TO REDUCE BONE LOSS

[75] Inventors: Lorne M. Golub; Nangavarum S. Ramamurthy, both of Smithtown; Thomas F. McNamara, Port Jefferson; Robert A. Greenwald, Melville, all of N.Y.

[73] Assignee: The Research Foundation of State University of New York, Albany, N.Y.

[21] Appl. No.: 200,415

[22] Filed: Feb. 23, 1994

Related U.S. Application Data

[63] Continuation of Ser. No. 743,579, Aug. 12, 1991, Pat. No. 5,321,017, which is a continuation of Ser. No. 445,410, Dec. 4, 1989, abandoned.

[51] Int. Cl.$^6$ .......................... A61K 31/65; A61K 31/19; A61K 31/40
[52] U.S. Cl. .......................... 514/152; 514/570; 514/557; 514/420; 514/825
[58] Field of Search .................... 514/570, 152, 514/557, 420, 825

[56] References Cited

U.S. PATENT DOCUMENTS

| | | | |
|---|---|---|---|
| 3,304,227 | 2/1967 | Loveless | 167/53.1 |
| 3,787,324 | 1/1974 | Zinnes et al. | 260/243 R |
| 4,049,700 | 9/1977 | Sinkula | 514/152 |
| 4,189,497 | 2/1980 | Hanifin et al. | 424/275 |
| 4,218,449 | 8/1980 | Wyburn-Mason | 424/248.4 |
| 4,269,832 | 5/1981 | Tomcufcik et al. | 424/422 |
| 4,666,897 | 5/1987 | Golub et al. | 514/152 |
| 4,677,132 | 6/1987 | Hayward | 514/411 |
| 4,704,383 | 11/1987 | McNamara et al. | 514/152 |
| 4,925,833 | 5/1990 | Golub et al. | 514/152 |
| 4,935,411 | 6/1990 | McNamara et al. | 514/152 |
| 4,935,412 | 6/1990 | McNamara et al. | 514/152 |
| 5,045,538 | 9/1991 | Schneider et al. | 514/152 |

OTHER PUBLICATIONS

Hall, C. M., "Flurbiprofen: Chemistry And Biology", *Effect Of Flurbiprofen On Bone Metabolism: Clinical And Laboratory Updates;* Monograph, Upjohn Co., Inc. (1988).
Golub, et al., "Further Evidence That Tetracyclines Inhibit Collagenase Activity In Human Crevicular Fluid And From Other Mammlian Sources", *J. Periodont. Res.* 20, 12–23 (1985).
Greenwald, et al., "Direct Detection Of Collagenase And Gelatinase In Periarticular Tissue From Adjuvant Arthritic Rats: Inhibition By Tetracyclines And Potential Amelioration Of Bone Destruction", Abstract, *Transactions Of The Orthopedic Research Society,* vol. 15 p. 270 (1990).
*The Chemistry of Tetracyclines,* (L. A. Mitscher, ed.) Chapter 6, 165–218 (1978).
Golub, et al., "Tetracyclines (TCs Inhibit Metalloproteinases (MPs): In Vivo Effects In Arthritic And Diabetic Rats, And New In Vitro Studies", Abstract, Matrix Metalloproteinase Conference, p. 43, Sep., 1989.
Sipos, et al., "The Effect Of Collagenase Inhibitors on Alveolar Bone Loss Due to Periodontal Disease In Desalivated Rats", Abstract, Matrix Metalloproteinase Conference, p. 43, Sep., 1989.
Breedveld, et al., "Suppression Of Collagen And Adjuvant Arthritis By A Tetracycline", Abstract, Northeastern Regional Meeting Of The Amer. Rheum. Assoc., p. 17, Oct., 1987.
Elewski, et al., "In Vivo Suppression Of Neutrophil Chemotaxis By Systemically And Topically Administered Tetracycline", *Journal of the American Academy of Dermatology* 8, 807–812 (1983).
Skinner, et al., "Tetracycline In The Treatment Of Rheumatoid Arthritis—A Double Blind Controlled Study", *Arthritis and Rheumatism* 14:6, 727–732 (1971).
Plewig, et al., "Anti–inflammatory Effects Of Antimicrobial Agents: An In Vivo Study", *Journal of Investigative Dermatology* 65, 532–536 (1975).
White, J. E., "Minocycline For Dystrophic Epidermolysis Bullosa", *Lancet,* 966 (1989).
Delaissé, et al., "A New Synthetic Inhibitor Of Mammalian Tissue Collagenase Inhibits Bone Resorption In Culture", *Biochemical and Biophysical Research Communications* 133, 483–490 (1985).
Cowen, et al., "Monensin Inhibits Collagenase Production In Osteoblastic Cell Cultures And Also Inhibits Both Collagenase Release And Bone Resorption In Mouse Calvaria Cultures", *Biochemistry International* 11, 273–280 (1985).
Wong, et al., "Oral Ibuprofen And Tetracycline For The Treatment Of Acne Vulgaris", *Journal of the American Academy of Dermatology* 11, 1076–1081 (1984).
Funt, L. S., "Oral Ibuprofen And Minocycline For The Treatment Of Resistant Acne Vulgaris", *Journal of the American Academy of Dermatology* 13, 524–525 (1985).
Golub, et al., "A Non–antibacterial Chemically–modified Tetracycline Inhibits Mammalian Collagenase Activity", *J. Dent. Res.* vol. 66(8), 1310–1314, Aug., 1987.
Breedveld, et al., "Minocycline Treatment For Rheumatoid Arthritis: An Open Dose Finding Study", *The Journal Of Rheumatology* 17:1 (1990).
Greenwald, et al., "Tetracyclines Suppress Matrix Metalloproteinase Activity In Adjuvant Arthritis And In Combination With Flurbiprofen, Ameliorate Bone Damage", *J. Rheum.* 19:6 (1992).

*Primary Examiner*—Marianne M. Cintins
*Assistant Examiner*—T. J. Criares
*Attorney, Agent, or Firm*—Hoffmann & Baron

[57] ABSTRACT

A method for treating mammals suffering from rheumatoid arthritis and other tissue-destructive (chronic inflammatory or other) conditions associated with excess metalloproteinase activity comprising administering to the mammal an amount of a tetracycline that is effectively anti-metalloproteinase, but that is not effectively antimicrobial, and an amount of non-steroidal anti-inflammatory agent which, when combined with the effectively anti-metalloproteinase amount of tetracycline, results in a significant reduction of tissue destruction and/or bone loss.

4 Claims, 1 Drawing Sheet

COMPOSITION COMPRISING INDOMETHACIN [NON-STEROIDAL ANTI-INFLAMMATORY AGENT] AND EFFECTIVELY NON-ANTIBACTERIAL TETRACYCLINE TO REDUCE BONE LOSS

The present application is a continuation of application Ser. No. 07/743,579 filed on Aug. 12, 1991, now U.S. Pat. No. 5,321,017, which is a continuation of Ser. No. 07/445,410 filed on Dec. 4, 1989, now abandoned.

The present invention relates to an anti-collagenolytic composition useful in the treatment of rheumatoid arthritis and other tissue-destructive conditions associated with excess collagenolytic activity as well as a method for using such formulations.

BACKGROUND OF THE INVENTION

Tetracyclines constitute a family of well known natural and synthetic broad spectrum antibiotics. The parent compound, tetracycline, exhibits the following general structure:

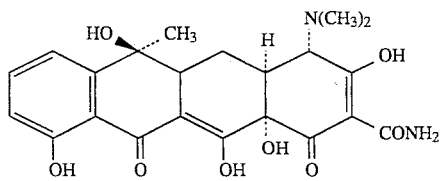

The numbering system of the ring nucleus is as follows:

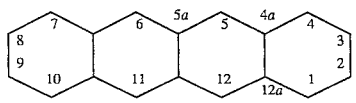

Tetracycline as well as the 5-OH (terramycin) and 7-Cl (Aureomycin) derivatives exist in nature, and are well known antibiotics. Natural tetracyclines may be modified without losing their antibiotic properties, although certain elements of the structure must be retained. The modifications that may and may not be made to the basic tetracycline structure have been reviewed by Mitscher in The Chemistry of Tetracyclines, Chapter 6. According to Mitscher, the substituents at positions 5–9 of the tetracycline ring system may be modified without the complete loss of antibiotic properties. Changes to the basic ring system or replacement of the substituents at positions 1–4 and 10–12, however, generally lead to synthetic tetracyclines with substantially less or effectively no antibacterial activity. For example, 4-dedimethylaminotetracycline is commonly considered to be a non-antibacterial tetracycline.

The use of tetracycline antibiotics, while effective, may lead to undesirable side effects. For example, the long term administration of antibiotic tetracyclines may reduce or eliminate healthy flora, such as intestinal flora, and may lead to the production of antibiotic resistant organisms or the overgrowth of yeast and fungi.

In addition to their antibiotic properties, tetracyclines are also known to inhibit the activity of collagen destructive enzymes such as mammalian collagenase, macrophage elastase and bacterial collagenase; Golub et al., *J. Periodont. Res.* 20, 12–23 (1985) and Golub, et al., *J. Periodont. Res.* 1989, submitted for publication. Collagen is a major component of connective tissue matrices such as those in bone, synovium, eye, skin, tendons and gingiva. Collagenase, which is naturally produced by only a few types of bacteria and in a number of tissues and cells in mammals, degrades collagen.

The degradation of collagen by mammalian collagenase is a natural part of the normal growth-degradation-regeneration process that occurs in connective tissue. The production of collagenase, however, may become excessive. Such excessive collagenase production often results in the pathologic and debilitating destruction of connective tissue.

U.S. Pat. No. 4,704,383 to McNamara et al. discloses that tetracyclines having substantially no effective antibacterial activity inhibit collagenolytic enzyme activity in rats. McNamara et al. also report that non-antibacterial tetracyclines reduce bone resorption in organ culture, although no clinical studies were reported.

Earlier, U.S. Pat. No. 4,666,897 to Golub, et al. disclosed that tetracyclines in general, including commercially-available antimicrobial forms of the drug, inhibit excessive bone resorption.

There have been a number of suggestions that tetracyclines, including non-antibacterial tetracyclines, are effective in treating arthritis in rats. See, for example, Golub et al. "Tetracyclines (TCs) Inhibit Metalloproteinases (MPs): In Vivo Effects In Arthritic And Diabetic Rats, And New In Vitro Studies," abstract presented at Matrix Metalloproteinase Conference, Destin, Fla., Sep. 11–15, 1989; Breedveld, "Suppression Of Collagen And Adjuvant Arthritis By A Tetracycline," Northeastern Regional Meeting Of The Amer. Rheum. Assoc., Atlantic City, N.J., Oct. 23–24, 1987. For related commentary regarding the effect of non-antibacterial tetracyclines on bone loss see Sipos et al., "The Effect Of Collagenase Inhibitors On Alveolar Bone Loss Due To Periodontal Disease In Desalivated Rats," abstract presented at Matrix Metalloproteinase Conference, Destin, Fla., Sep. 11–15, 1989.

An effect of tetracyclines independent of antibiotic effects has, however, not been established for human patients with rheumatoid arthritis. Thus, Skinner et al., *Arthritis and Rheumatism* 14, 727–732 (1971), reported no significant benefit from tetracycline therapy for human sufferers of rheumatoid arthritis even though Greenwald et al., reported in *J. Rheumatol.* 14: 28–32 (1987) that the oral administration of a tetracycline to humans with severe rheumatoid arthritis decreased the collagenase activity in the joint tissues.

It is known that, unlike tetracyclines, non-steroidal anti-inflammatory agents are useful in the symptomatic treatment of rheumatoid arthritis as well as other inflammatory diseases. Such agents, however, do not effectively prevent long term destruction of joint-connective tissues including tendons, cartilage and bone caused by the presence of excessive amounts of collagenase.

Excessive collagenase activity has also been implicated in certain skin disorders. According to White, Lancet, Apr. 29th, 1989, p. 966 (1989) the tetracycline minocycline is effective in treating dystrophic epidermolysis bullosa, which is a life-threatening skin condition believed to be related to excess collagenase.

The effectiveness of tetracycline in skin disorders has also been studied by Elewski et al., *Journal of the American Academy of Dermatology*, 8, 807–812 (1983). Elewski et al. disclosed that tetracycline antibiotics may have anti-inflammatory activity in skin and speculate that a portion of the therapeutic effect in skin diseases associated with bacteria, e.g., acne, may be due to inhibition of bacterially induced inflammation rather than a direct anti-bacterial effect.

Similarly, Plewig et al., Journal of Investigative Dermatology 65, 532–532 (1975), disclose experiments designed to test the hypothesis that anti-microbials are effective in treating inflammatory dermatoses. The experiments of Plewig et al. establish that tetracyclines have anti-inflammatory properties in treating pustules induced by potassium iodide patches.

There has also been speculation that collagenase is involved in bone resorption. For example, Cowen et al., *Biochemistry International* 11, 273–280 (1985), hypothesize that osteoblast production of collagenase might be an initiating event in bone resorption, leaving minerals to be phagocytosed by osteoclasts.

Further, Dellaissé et al., *Biochemical and Biophysical Research Communications* 133, 483–490 (1985), propose that collagenase plays a critical role in bone resorption. The work of Dellaissé et al., shows that inhibition of mammalian collagenase and related tissue metallo-proteinases prevent the degradation of bone collagen, thus inhibiting the resorption of explanted mouse bones in tissue culture.

The use of tetracyclines in combination with non-steroidal anti-inflammatory agents has been studied in the treatment of inflammatory skin disorders caused by acne vulgaris. Wong et al., *Journal of American Academy of Dermatology* 11, 1076–1081 (1984), studied the combination of tetracycline and ibuprofen and found that tetracycline was an effective agent against acne vulgaris while ibuprofen was useful in reducing the resulting inflammation by inhibition of cyclooxygenase. Funt, *Journal of the American Academy of Dermatology* 13, 524–525 (1985), disclosed similar results by combining the tetracycline minocycline and ibuprofen.

In most of the above studies, the tetracycline was believed to be useful for its antibiotic effect. Therefore, with the exception of the disclosure in the McNamara et al. patent, antibacterial tetracyclines were used despite their undesirable side effects.

Despite the above studies, an effective long term treatment for rheumatoid arthritis and other tissue-destructive conditions associated with excess collagenolytic activity has remained elusive. It is an object of this invention to provide such a treatment. Another object of this invention is to provide such a treatment while avoiding the side effects of antibacterial tetracycline therapies.

SUMMARY OF THE INVENTION

It has now been discovered that these and other objectives can be achieved by providing a method for treating mammals suffering from rheumatoid arthritis and other tissue-destructive conditions associated with excess metalloproteinase activity which includes administering to the mammal an amount and/or type of a tetracycline that is effectively anti-metalloproteinase, but that is not effectively antimicrobial, and an amount of non-steroidal anti-inflammatory agent which, when combined with the effectively anti-metalloproteinase amount and/or type of tetracycline, results in a significant reduction of bone loss. The invention further provides a pharmaceutical composition for treating mammals suffering from rheumatoid arthritis and other tissue-destructive conditions associated with excess metalloproteinase activity comprising (a) an amount of a tetracycline that is effectively anti-collagenase but that is not effectively anti-microbial; and (b) an amount of a non-steroidal anti-inflammatory agent which, when combined with the effectively anti-collagenase amount of tetracycline, results in a significant reduction of bone loss. The amount of tetracycline used in the present invention is that which is effectively non-antibacterial in the patient. Thus, tetracyclines generally used for anti-bacterial properties can also be used herein in reduced amounts which are effectively non-antibacterial.

DETAILED DESCRIPTION OF THE INVENTION

Figure 1:
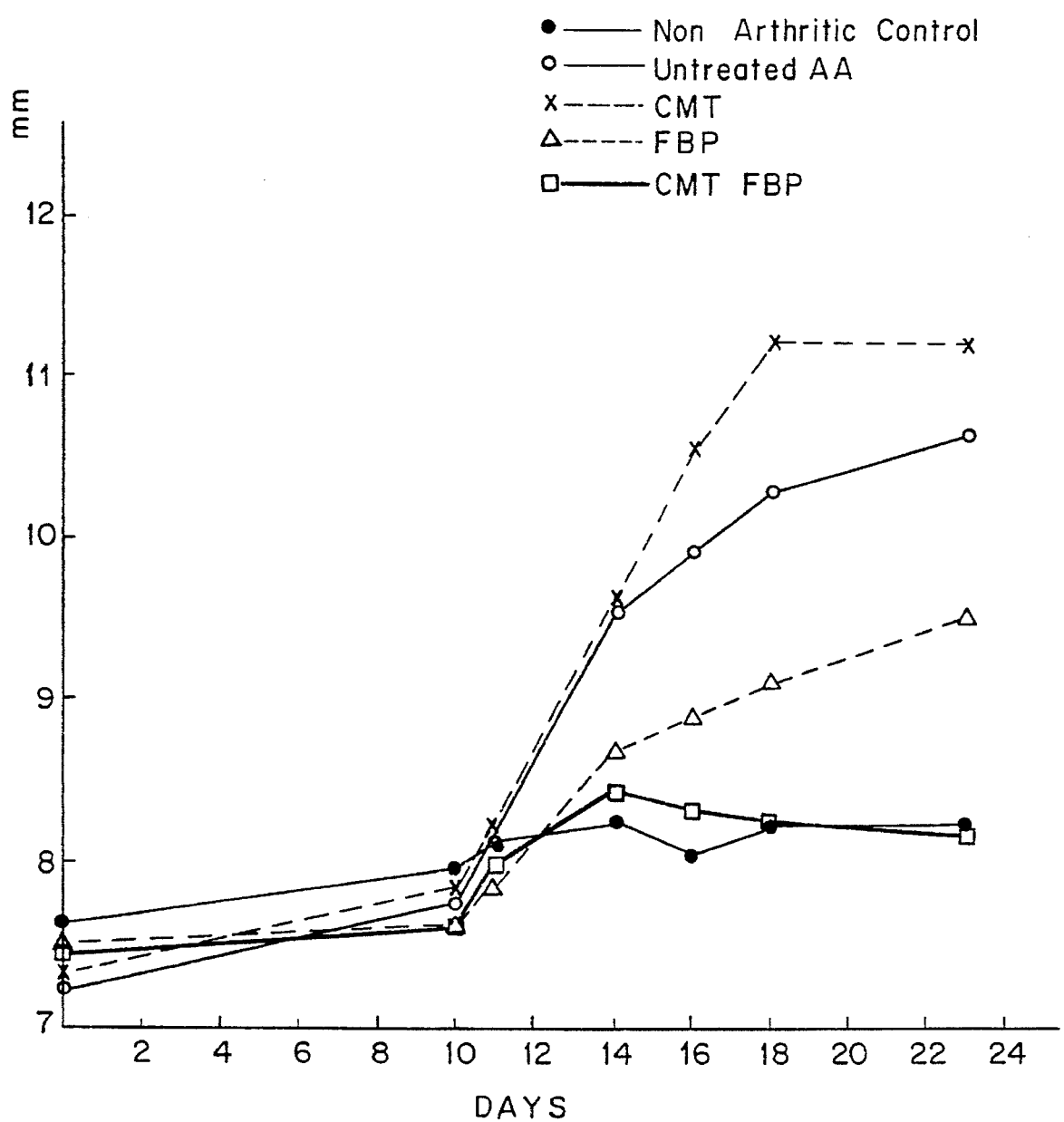
FIG. 1 dramatically depicts the unexpectedly excellent inflammation treatment characteristics achieved by use of the present invention.

The present invention is directed to the treatment of tissue-destructive conditions associated with excess activity of matrix-degrading proteinases such as the metalloproteinases. Typical metalloproteinases include, for example, collagenase and gelatinase. Tissue-destructive conditions treated in accordance with the present invention include (but is not limited to) rheumatoid arthritis, corneal ulceration, epipdermolysis bullosa, metabolic bone diseases including osteoporosis, disorders involving damage to basement membranes such as diabetic renal disease, disorders involving cellular passage through basement membranes such as metastic cancer, and periodontal diseases.

The conditions treated by the present invention occur in mammals. Mammals include, for example, human beings and laboratory animals such as mice and rats.

Reports that chemically modified non-antimicrobial tetracycline analogs inhibit metalloproteinases in vivo in rats; that chemically modified tetracyclines reduced alveolar bone loss associated with periodontal disease in desalivated rats; that antimicrobial and non-antimicrobial tetracylines inhibit bone resorption in tissue culture; that the tetracycline minocycline reduced the incidence and severity of arthritis in rats; and that antibacterial tetracyclines reduce bone resorption in vivo (Golub et al., U.S. Pat. No. 4,666,897) suggest that administration of non-antimicrobial doses of tetracyclines are expected to reduce bone loss in arthritic animals. The present inventors have unexpectedly found, however, that this is not the case. When arthritic rats were treated with non-antimicrobial doses of the chemically modified tetracycline 4-dedimethylaminotetracycline, there was no significant reduction in bone loss.

Also unexpectedly, the present inventors have found that bone loss is significantly reduced when mammals suffering from arthritis are treated with an amount of a tetracycline that is effectively anti-metalloproteinase but that is not effectively antimicrobial in combination with a non-steroidal anti-inflammatory agent. Bone loss may be reduced either by the prevention of bone resorption or stimulation of new bone formation.

The tetracycline may be any tetracycline administered to a mammal in a dose that is effectively non-antimicrobial in the mammal. Preferably, the tetracycline is modified so as to reduce its antimicrobial properties. Methods for reducing the anti-microbial properties of a tetracycline were disclosed in "The Chemistry of the Tetracyclines", Chapter 6, Mitscher, Ed. at page 211. As pointed out by Mitscher, modification at positions 1, 2, 3, 4, 10 and 12a lead to loss of bioactivity. The use of such modified tetracyclines is preferred in the present invention, since they can be used at higher levels than anti-microbial tetracyclines with fewer side effects.

The preferred tetracyclines are those that lack the dimethylamino group at position 4. Such chemically modified tetracyclines include, for example, 4-dedimethylaminotetracycline, 4-dedimethylamino-5-oxytetracycline, 4-dedimethylamino-7-chlorotetracycline, 4-hydroxy-4-dedimethylaminotetracycline, 5a,6-anhydro-4-hydroxy-4-dedimethylaminotetracycline, 6-demethyl-6-deoxy-4-dedimethylaminotetracycline, and 6-α-deoxy-5-hydroxy-4-dedimethylaminotetracycline.

Also tetracyclines altered at the 2 carbon position to produce a nitrile, e.g., tetracyclinotrile are useful as non-antimicrobial anti-metalloproteinase agents.

Further examples of tetracyclines modified for reduced anti-microbial activity include 6-α-benzylthiomethylenetetracycline, the 2-nitrilo analog of tetracycline, the mono-N-alkylated amide of tetracycline, 6-fluoro-6-demethyltetracycline, or 11α-chlorotetracycline.

The amount of tetracycline is an amount that is effectively anti-collagenase while not effectively antimicrobial. An amount of a tetracycline is effectively anti-collagenase if it significantly reduces anti-collagenase activity. A tetracycline is not effectively anti-microbial if it does not significantly prevent the growth of microbes. The maximal dosage for humans is the highest dosage that does not cause side effects. For example, the non-antimicrobial tetracycline may be administered in an amount of from about 0.1 mg/kg/day to about 24 mg/kg/day and preferably from about 2 mg/kg/day to about 18 mg/kg/day. For the purpose of the present invention, side effects include clinically significant anti-microbial activity, as well as toxic effects. For example, a dose in excess of about 50 mg/kg/day would likely produce side effects in most mammals, including humans.

The non-steroidal anti-inflammatory agent may be selected from the various classes of such compounds. Such classes include, for example, salicylates such as acetylsalicyclic acid and diflunisal; acetic acids such as indomethacin, sulindac, tolmetin, diclofenac, and etodolac; propionic acids such as flurbiprofen, naproxen, and ketoprofen; fenamates such as meclofenamate; and oxicams such as piroxicam.

The preferred non-steroidal anti-inflammatory agents include flurbiprofen, piroxicam, tolmetin sodium, ibuprofen, naproxen and indomethacin.

The amount of the non-steroidal anti-inflammatory agent is an amount which, when combined with the effectively anti-collagenase amount of tetracycline, results in a significant reduction of bone loss in mammals suffering from tissue-destructive conditions associated with excess metalloproteinase activity. The amount depends on the particular anti-inflammatory agent used, the mammal to which the composition is administered, and the amount of the tetracycline in the composition. Some typical doses for routine human use include, for example, 20 mg/day for piroxicam, 150 mg/day for indomethacin, 1600–1800 mg/day for tolmetin, 1000 mg/day for naproxen, and 3200 mg/day for ibuprofen.

For example, a suitable amount of 4.dedimethylamino tetracycline is 15 mg/kg. A suitable amount of anti-inflammatory agent in combination with 30 mg/kg 4-dedimethylamino tetracycline would be, for example, 1–8 mg/kg flurbiprofen, 0.3 mg/kg piroxicam and 40 mg/kg ibuprofen.

As a guideline for providing the proper amount of anti-inflammatory agents for implementing the present invention, a rule of thumb is to administer an amount which is 20% to 80% of the conventional anti-inflammatory dose for treating arthritis. Thus, the dosage could be from as small as 10 mg/person/day for piroxicam, to as great as 3200 mg/person/day for ibuprofen. In any event, the practitioner is guided by skill and knowledge in the field and the present invention includes without limitation dosages which are effective to achieve the described phenomenon. For example, the non-steroidal anti-inflammatory agent may be administered in an amount of from about 0.3 mg/kg/day to about 3500 mg/kg/day.

The preferred pharmaceutical composition for use in the present invention comprises a combination of the tetracycline and the anti-inflammatory agent in a suitable pharmaceutical carrier. The means of delivery of the pharmaceutical carrier with active may be in the form of a capsule, compressed tablet, pill, solution or suspension suitable for oral administration to a mammal. Other means of delivery include a gel for topical application for corneal ulcers, periodontal disease, etc. It is contemplated that carriers be included which are suitable for administration orally, topically, by injection into a joint, and by other selected means.

EXAMPLES OF THE INVENTION

EXAMPLE I

The following experiment was carried out to determine the effect of a non-steroidal anti-inflammatory drug (flurbiprofen), a chemically modified non-antimicrobial tetracycline (4-dedimethylaminotetracycline; CMT), and a flurbiprofen/CMT combination on: (i) the collagenase and gelatinase activities, (ii) the severity of inflammation assessed clinically, and (iii) the loss of bone assessed by radiographs in the tissues and joints of rats with experimental arthritis.

Thirty-six adult Lewis rats were made arthritic by injection of Freund's adjuvant and the animals distributed into the following experimental groups: Group I—untreated arthritic rats; Group II—arthritic rats administered flurbiprofen daily by oral gavage (1.0 mg per rat); Group III—arthritic rats administered CMT daily by oral gavage (3 mg per rat); Group IV—arthritic rats administered both drugs. After a 2–3 week experimental period (2 weeks for the 6 rats/group assessed for enzyme activity; 3 weeks for the 3 rats/group assessed for enzyme activity; 3 weeks for the 3 rats/group assessed by x-rays for bone loss), the rats were killed, the hind paws obtained, the skin removed and the inflamed subcutaneous tissues overlying the arthritic joints were dissected (all dissection and extraction procedures at 4° C.). The tissues were minced, weighed, extracted, and the extracts partially purified by ammonium sulfate precipitation using techniques described Freviously (Ramamurthy and Golub, *J. Periodontal Res.* 17, 455, (1983)). The extracts of the diseased tissue were then concentrated 5-fold and aliquots were incubated (a) with [$^3$H-methyl] gelatin (denatured type I rat skin collagen) at 37° C. for 4 hours to measure gelatinase activity. The undigested gelatin was precipitated with trichloroacetic acid and, after centrifugation, aliquots of the degradation products in the supernatants were measured in a liquid scintillation spectrometer; (b) for the collagenase assay, the extracts were incubated with [$^3$H-methyl] collagen for 18 hours at 22° C. and the radiolabeled collagen components (α chains) and degradation fragments ($α^A$) were assessed by a combination of SDS-polyacrylamide gel electrophoresis & fluorography as described previously (Golub et al. *J. Periodontal Res.* 20, 12 (1985).

Results

1. The untreated arthritic rats showed the highest level of tissue-destructive metalloproteinase activity (gelatinolytic and collagenolytic) which was associated with the most inflammatory swelling of the paws and the most bone loss in the joints, the latter assessed by x-rays.

2. The arthritic rats treated with flurbiprofen alone showed a reduction in swelling of the paws, a slight reduction in metalloproteinase activity (although the reduction in gelatinolytic activity was not statistically significant; Note—collagenolytic activity assessed by fluorography was not analyzed statisically), and slight reduction of bone loss in the joints.
3. The arthritic rats treated with CMT alone showed a significant reduction in metalloproteinase activity, a slight reduction in joint bone loss, and no detectable anti-inflammatory effect (no detectable reduction in paw swelling).
4. The arthritic rats treated with CMT plus flurbiprofen showed complete inhibition of collagenolytic and the greatest reduction of gelatinolytic activity; the greatest reduction of bone loss in the joints; and a reduction in paw swelling as great or greater than observed with flurbiprofen alone.

TABLE I

THE EFFECT OF FLURBIPROFEN OR CMT ALONE, OR THE TWO COMBINED, ON GELATINOLYTIC ACTIVITY IN INFLAMED ARTHRITIC RAT PAW TISSUE*

| | Experimental Group | %[$^3$H-Methyl] Gelatin Degraded | Statistical Significance vs. Group I |
|---|---|---|---|
| I. | (Untreated Arthritics) | 76.2 ± 1.4 | — |
| II. | (Arthritics + Flurbiprofen) | 68.3 ± 3.2 | Not significant; $p > 0.05$ |
| III. | (Arthritics + CMT) | 52.2 ± 4.9 | Significant; $p < 0.01$ |
| IV. | (Arthritics + Both Drugs) | 45.6 ± 3.4 | Significant; $p < 0.01$ |

*Each value represents the mean ± S.E.M. for 6 rats/group.

From the above results, one can conclude that the treatment of arthritic rats with CMT alone or with flurbiprofen alone each produced some amelioration of the pathologic joint changes. However, treatment of the arthritis with the two drugs combined produced the greatest reduction of the tissue-destructive inflammatory joint changes.

EXAMPLE II

Yet a further experiment was conducted to determine the efficacy of the invention by comparing results achieved using chemically modified non-antibacterial tetracycline (4-dedimethylaminotetracycline) alone, the non-steroidal anti-inflammatory drug flurbiprofen and a combination of flurbiprofen and CMT on arthritically-induced bone and joint destruction. In order to conduct the experiment, the investigators used adult Lewis rats having a starting body weight of about 120 grams each. The rats were distributed into five groups which included one six-rat control group which was not injected to induce arthritis, and forty-eight adult Lewis rats which were made arthritic by injection of Freund's adjuvant. The arthritic rats were distributed into the following experimental groups: Group I—untreated arthritic rats were orally administered vehicle alone, i.e., 2% carboxymethylcellulose; Group II—arthritic rats treated on a daily basis by oral intubation with the chemically modified tetracycline (CMT) at a dosage rate of 4 mg/day per rat; Group III—arthritic rats treated daily by oral intubation with the non-steroidal anti-inflammatory drug flurbiprofen (at a rate of 0.5 mg/day per rat); Group IV—arthritic rats treated with a combination of CMT plus the flurbiprofen in the doses previously described with respect to treatment with the single active ingredient.

Twenty-three days after inducing arthritis, half of the rats in each group were sacrificed. The hind paws were disected and radiographs of the bones and joints were taken using high-sensitivity x-ray film. The x-rays were scored, in a blinded fashion, by two independent experienced examiners, to assess the severity of arthritic bone destruction in the five different groups of rats. The scores were given in accordance with the following scale: 1=normal, 2=mild, 3=moderate, and 4=severe bone destruction. An additional experienced examiner scored the results after the initial examination The results have been set forth in Table II.

TABLE II

| Experimental Group | Bone Destruction Score | Serum concentration of CMT (μg/ml)* |
|---|---|---|
| Non-arthritic controls | 1.0 | 0 ± 0 |
| Arthritics + vehicle | 2.8 | 0 ± 0 |
| Arthritics + CMT | 2.4 | 12.8 ± 0.5 (SEM) |
| Arthritics + flurbiprofen | 2.0 | 0 ± 0 |
| Arthritics + combination | 1.1 | 12.4 ± 1.3 (SEM) |

*The serun data was obtained from rats sacrificed on day 14.

The data above represents the average score for the three examiners for six bones per group, except that five bones were used for the group treated with the combination of CMT and NSAID.

Results

1. Each of the active ingredients, CMT and the flurbiprofen used alone had only slight inhibitory effects on the arthritically induced bone and joint destruction during the twenty-three day protocol. This result is quite surprising in view of the earlier beliefs, as set forth in the literature, which led the investigators to expect that each of the ingredients might separately be effective.
2. The combination of CMT and flurbiprofen exhibited an inordinately potent ability to prevent bone and joint destruction in rats which had been arthritically induced during the experiment.
3. Further information gathered from the results of this experiment show that the oral administration of flurbiprofen in combination with CMT did not reduce the blood level of CMT.

Further data was gathered by making physical measurements of the paw diameters before and during the protocol to determine the degree of inflammation. The results shown in FIG. 1 clearly depict a dramatic reduction in the inflammation as a result of the combined use CMT and flurbiprofen.

In fact, the combination of CMT and flurbiprofen administered to arthritic rats produced paw diameter scores essentially identical to the scores obtained from the normal non-arthritic rats. The paws taken from the rats treated with CMT alone show high inflammation. Paws taken from rats subjected to flurbiprofen treatment alone, on the other hand, produced a distinct anti-inflammatory effect, as expected. The untreated paws from the arthritic rats displayed expected normal inflammatory paw diameter measurements. This is a dramatic showing of the efficacy of the combined actives.

Basically, the results of the second experiment confirm the results of the first experiment, and also dramatize the potential effectiveness of the present invention in treatment of tissue-destructive conditions.

Thus, while there have been described what at presently believed to be the preferred embodiments of the present invention other changes and further modifications will become apparent to one skilled in the art, and it is intended to include all such changes and modifications as come within the spirit of the present invention.

What we claim is:

1. A method for treating mammals suffering from bone loss comprising administering to the mammal 4-dedimethylaminotetracycline in a synergistic amount which is effective as an anti-metalloproteinase and a synergistic amount of indomethacin, which, when combined with the effectively anti-metalloproteinase tetracycline, results in a synergistic reduction of bone loss.

2. The method according to claim 1 wherein said tetracycline is administered in an amount of from about 0.1 mg/kg/day to about 24 mg/kg/day and said indomethacin is administered in an amount of from about 0.3 mg/kg/day to about 3500 mg/kg/day.

3. The method according to claim 2 wherein said indomethacin is present in an amount of from about 20% to about 80% of the conventional anti-inflammatory dose used for treating arthritis.

4. The method according to claim 3 wherein said tetracycline is administered in an amount of from about 2 mg per kg per day to about 18 mg per kg per day.

* * * * *